(12) United States Patent
Lensbouer

(10) Patent No.: US 9,096,512 B2
(45) Date of Patent: Aug. 4, 2015

(54) METHODS FOR PREPARING METHACRYLIC ACID FROM BIOBASED STARTING MATERIALS

(71) Applicant: ARMSTRONG WORLD INDUSTRIES, INC., Lancaster, PA (US)

(72) Inventor: Joshua Lensbouer, Mt. Joy, PA (US)

(73) Assignee: AWI Licensing Company, Wilmington, DE (US)

( * ) Notice: Subject to any disclaimer, the term of this patent is extended or adjusted under 35 U.S.C. 154(b) by 0 days.

(21) Appl. No.: 14/487,281

(22) Filed: Sep. 16, 2014

(65) Prior Publication Data

US 2015/0080606 A1    Mar. 19, 2015

Related U.S. Application Data

(60) Provisional application No. 61/878,501, filed on Sep. 16, 2013.

(51) Int. Cl.
| | | |
|---|---|---|
| *C07C 51/377* | (2006.01) | |
| *C07C 51/295* | (2006.01) | |
| *C07C 51/363* | (2006.01) | |
| *C07C 69/54* | (2006.01) | |
| *C07C 51/16* | (2006.01) | |

(52) U.S. Cl.
CPC ............... *C07C 51/377* (2013.01); *C07C 51/16* (2013.01); *C07C 51/295* (2013.01); *C07C 51/363* (2013.01); *C07C 69/54* (2013.01)

(58) Field of Classification Search
None
See application file for complete search history.

(56) References Cited

U.S. PATENT DOCUMENTS

| | | |
|---|---|---|
| 4,543,422 A | 9/1985 | Farrar |
| 5,362,904 A | 11/1994 | Kearns |
| 6,146,711 A | 11/2000 | Courtoy et al. |
| 8,455,683 B2 | 6/2013 | Burk et al. |
| 2011/0124829 A1 | 5/2011 | Alarifi et al. |
| 2011/0190464 A1 | 8/2011 | Dubois et al. |

FOREIGN PATENT DOCUMENTS

WO    2008/007002 A2    1/2008

OTHER PUBLICATIONS

Database Reaxys, Database accession No. 210444, Bulletin de la Societe Chimique de France, vol. <4>5, p. 921 (XP-002735341) (1909) FR (Abstract).
Salkind Y.S. et al., "Obtaining of Methacrylic Acid Esters of Isobutyric Acid", Zhurnal Prikladnoi Khimii, Maik Nauka: Rossiiskaya Akademiya Nauk, RU., vol. 10, Jan. 1, 1937, pp. 1042-1044, XP008174583 RU.
Search Report dated Mar. 6, 2015, for corresponding EP Application No. 14184815.0, filed Sep. 15, 2014.

*Primary Examiner* — Karl J Puttlitz
(74) *Attorney, Agent, or Firm* — Michael U. Lee

(57) ABSTRACT

Described herein are methods for preparing methacrylic acid from biobased starting materials.

15 Claims, No Drawings

METHODS FOR PREPARING METHACRYLIC ACID FROM BIOBASED STARTING MATERIALS

CROSS-REFERENCE TO RELATED APPLICATION

This application claims the benefit of priority from U.S. Provisional Application Ser. No. 61/878,501, filed 16 Sep. 2013, the contents of which are hereby incorporated herein in their entirety.

FIELD

Embodiments of the present invention relate to methods for preparing methacrylic acid from biobased starting materials.

BACKGROUND

Methacrylate esters are polymerized to make polymethyl methacrylate acrylic plastic homopolymers, and can also polymerize with other monomers to form copolymers useful as acrylic sheets, molding compounds, resins and latexes for use in coatings, adhesives, waxes, polishes, and thermosetting automotive/appliance enamels. Historically, methacrylate ester monomers have been made from certain petroleum-derived compounds. However, such petroleum-derived monomers are frequently expensive because of fluctuations in the pricing and availability of petroleum, and are increasingly likely to remain so as petroleum reserves are reduced and new supplies prove more costly and difficult to secure. Further, in the context of methacrylate ester production, the use of hydrogen cyanide and the production of large amounts of ammonium sulfate by-product have raised concerns for process safety and byproduct disposal.

For example, methacrylic acid is currently produced via acetone cyanohydration. Acetone is directly tied to the production of phenol in the cumene process and is a petroleum based product. When phenol is not being produced, acetone is not being produced. Because its production is tied to the availability of other chemicals, the production of methacrylic acid fluctuates and creates potential instability, which hampers industries that utilize methacrylic acid.

These issues along with concerns over greenhouse gas emissions and consumer demand for more environmentally friendly products have sparked a shift from production of chemicals derived from petroleum sources to chemicals derived from sustainable materials, particularly biobased materials. However, challenges exist in the development of biobased materials, including: 1) adequate supply of starting materials; 2) competitive production processes; and 3) industry acceptance of a reduced number of alternatives. Despite these challenges, there is a need and desire for commercially suitable biobased chemicals. Specifically, the UV/EB curable industry stands to benefit from the availability of such materials.

Moreover, conventional methods of preparing biobased industrial chemicals have required complex processes having multiple steps, which increases both the time and cost of obtaining such materials. For example, the production of biobased 1,3-propanediol—an organic compound which has numerous uses across multiple industries—requires at least the following process steps: microfiltration and ultrafiltration, ion exchange, flash evaporation, and distillation. Accordingly, there remains a need for efficient and cost-effective processes, which produce high yields of biobased industrial chemicals. Embodiments of the present invention are designed to provide a solution to the above-described problems.

SUMMARY

In some embodiments, the present invention provides methods for preparing methacrylic acid, comprising the following steps:
a) oxidizing a compound of formula I

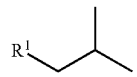

wherein $R^1$ is oxo or hydroxyl, to obtain an isobutyric acid;
b) halogenating the isobutyric acid to obtain 3-haloisobutyric acid; and
c) dehalogenating the 3-haloisobutyric acid to obtain methacrylic acid.

In some embodiments, the compound of formula I is selected from isobutanol and isobutanal.

In some embodiments, the present invention provides a flooring product comprising the product of any one of the processes described herein.

DETAILED DESCRIPTION

Some embodiments of the present invention provide a method for preparing methacrylic acid, comprising the following steps:
a) oxidizing a compound of formula I

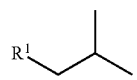

wherein $R^1$ is oxo or hydroxyl, to obtain an isobutyric acid;
b) halogenating the isobutyric acid to obtain 3-haloisobutyric acid; and
c) dehalogenating the 3-haloisobutyric acid to obtain methacrylic acid.

In some embodiments, $R^1$ is hydroxyl. In some embodiments, $R^1$ is oxo.

In some embodiments, the compound of formula I is selected from isobutanol and isobutanal.

In some embodiments, the oxidizing agent is selected from ozone, potassium permanganate, nitric acid, chromic acid and chromium trioxide. Metals and metal oxides with oxygen may also be used to catalyze conversion of the alcohol to a carboxylic acid. In some embodiments, the oxidizing agent is ozone.

In some embodiments, step b) is carried out in the presence of acetic anhydride.

In some embodiments, the isobutyric acid is halogenated a halogen selected from fluorine, chlorine, bromine, and iodine.

Some embodiments further comprise the step of purifying the methacrylic acid. In some embodiments, the methacrylic acid is purified by distillation.

In some embodiments, the compound of formula I is prepared by fermentation.

In some embodiments, the 3-haloisobutryic acid is dehalogenated using an inorganic base. In some embodiments, the inorganic base is selected from sodium hydroxide and potassium hydroxide. In some embodiments, the inorganic base is sodium hydroxide.

In some embodiments, the 3-haloisobutyric acid is selected from 3-fluoroisobutyric acid, 3-chloroisobutyric acid, 3-bromoisobutyric acid, and 3-iodoisobutyric acid.

Some embodiments of the present invention provide methods further comprising the step of esterifying the methacrylic acid to obtain a methacrylate ester.

Still further embodiments provide a coating for a substrate comprising a product of any one of the methods described herein. In some embodiments, the substrate is a flooring product. In some embodiments, the substrate is a tile. In some embodiments, the substrate is a sheet product. In some embodiments, the sheet product is a linoleum sheet product. In some embodiments, the substrate is selected from a linoleum the and a vinyl tile. In some embodiments, the vinyl tile is a luxury vinyl tile.

In some embodiments, the methods of the present invention follow the Scheme I described below:

Scheme I

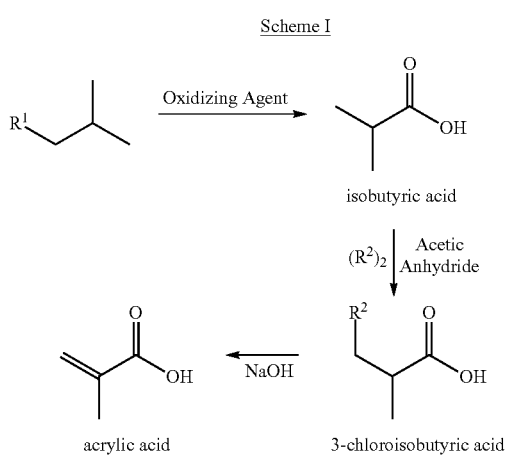

wherein $R^1$ is oxo or hydroxyl and $R^2$ is selected from fluorine, chlorine, bromine, and iodine.

The invention will be described in greater detail by way of specific examples. The following examples are offered for illustrative purposes and are not intended to limit the invention in any manner. Those skilled in the art will readily recognize a variety of noncritical parameters which can be changed or modified to yield essentially the same results.

EXAMPLES

Example 1

Isobutyric acid is made from isobutanol and isobutanal by using an oxidizing agent such as potassium permanganate. Aqueous potassium permanganate is added to isobutanol in a 2:1 molar ratio under room temperature conditions. Isobutyric acid is made by this reaction and the water can be distilled off at 100° C., followed by isobutyric acid distillation at 155° C. Isobutyric acid can also be solvent extracted and distilled for purification.

It is intended that any patents, patent applications or printed publications, including books, mentioned in this patent document be hereby incorporated by reference in their entirety.

As those skilled in the art will appreciate, numerous changes and modifications may be made to the embodiments described herein, without departing from the spirit of the invention. It is intended that all such variations fall within the scope of the invention.

The invention claimed is:
1. A method for preparing methacrylic acid, comprising the following steps:
  a) oxidizing a compound of formula I

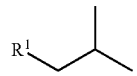

wherein $R^1$ is oxo or hydroxyl, to obtain isobutyric acid;
  b) halogenating the isobutyric acid to obtain 3-haloisobutyric acid; and
  c) dehalogenating the 3-haloisobutyric acid to obtain methacrylic acid wherein step b) is carried out in the presence of acetic anhydride.

2. The method of claim 1, wherein $R^1$ is oxo.

3. The method of claim 1, wherein $R^1$ is hydroxyl.

4. The method of claim 1, wherein the compound of formula I is selected from isobutanol and isobutanal.

5. The method of claim 1, wherein the oxidizing agent is selected from ozone, potassium permanganate, nitric acid, chromic acid and chromium trioxide.

6. The method of claim 5, wherein the oxidizing agent is potassium permanganate.

7. The method of claim 1, wherein the isobutyric acid is halogenated with a halogen selected from fluorine, chlorine, bromine, and iodine.

8. The method of claim 1, wherein the isobutyric acid is halogenated with chlorine.

9. The method of claim 1, further comprising the step of purifying the methacrylic acid.

10. The method of claim 9, wherein the methacrylic acid is purified by distillation.

11. The method of claim 1, wherein the compound of formula I is prepared by fermentation.

12. The method of claim 1, wherein the 3-haloisobutryic acid is dehalogenated using an inorganic base.

13. The method of claim 12, wherein the inorganic base is selected from sodium hydroxide and potassium hydroxide.

14. The method of claim 13, wherein the inorganic base is sodium hydroxide.

15. The method of claim 1, further comprising the step of esterifying the methacrylic acid to obtain a methacrylate ester.

* * * * *